United States Patent [19]

Yoshihama et al.

[11] Patent Number: 5,164,302

[45] Date of Patent: Nov. 17, 1992

[54] METHOD FOR PREPARING 7β-HYDROXY-4-PREGNENE-3,20-DIONE DERIVATIVES

[75] Inventors: Makoto Yoshihama, Utsunomiya; Koji Tamura, Shimotsuga; Nobuo Miyata; Masamichi Nakakoshi, both of Utsunomiya, all of Japan

[73] Assignee: Snow Brand Milk Products Company, Limited, Hokkaido, Japan

[21] Appl. No.: 436,582

[22] Filed: Nov. 15, 1989

Related U.S. Application Data

[62] Division of Ser. No. 294,567, filed as PCT/JP88/00115,. Feb. 5, 1988, Pat. No. 5,028,722.

[30] Foreign Application Priority Data

Feb. 6, 1987 [JP] Japan .................. 62-024597
Jun. 15, 1987 [JP] Japan .................. 62-147017

[51] Int. Cl.⁵ ............... C12P 33/00; C12P 33/12; C12P 33/06; C12N 1/14
[52] U.S. Cl. ............... 435/58; 435/52; 435/56; 435/911; 435/254
[58] Field of Search ............... 435/58, 52, 56, 911, 435/254

[56] References Cited

U.S. PATENT DOCUMENTS

| | | | |
|---|---|---|---|
| 2,879,280 | 3/1959 | Fried | 435/58 |
| 2,962,512 | 11/1960 | Bernstein | 435/58 |
| 3,031,477 | 4/1962 | Thoma | 435/58 |
| 3,125,495 | 3/1964 | Laskin | 43/58 |

OTHER PUBLICATIONS

ATCC Catalogue of Fungi, 1987, pp. 4–6.
ATCC Catalogue of Fungi, 1981, pp. 6 and 86.
Chem. Abstracts, vol. 55, No. 17, Aug. 21, 1961; Tsuda et al; "Microbiological hydroxylation of steroids". X. 7β,15β–dihydroxypregn–4–ene–3,20–dione.
Journal of Chemical Ecology, vol. 13, No. 1, Jan. 1987, pp. 35–38; Meinwald et al, "Defensive steroids from carrion beetle."

Primary Examiner—Irene Marx
Attorney, Agent, or Firm—Millen, White & Zelano

[57] ABSTRACT

Novel 7β-hydroxy-4-pregnene-3,20-dione derivatives are disclosed.

The group of these compounds has possibility of being utilizes as an intermediate for the synthesis of progesterone derivatives having ovulation-inhibiting activity. These compounds themselves have also cell differentiation activity for M1 cells.

2 Claims, 7 Drawing Sheets

FIG. I

METHOD FOR PREPARING 7β-HYDROXY-4-PREGNENE-3,20-DIONE DERIVATIVES

This is a division of application Ser. No. 07/294,567 filed as PCT/JP88/00115, Feb. 5, 1988 now U.S. Pat. No. 5,028,722.

TECHNICAL FIELD

This invention relates to novel pregnene derivatives used as intermediates for the synthesis of progesterone derivatives having ovulation-inhibiting activity. A group of these compounds is expected to be used in the field of medicine. Cell differentiation activity is also found on a part of these compounds and hence utilization as drugs is also expected in this area.

BACKGROUND ART

A variety of pregnene derivatives has already been found to date. However, pregnene derivatives of this invention are novel compounds and biological activities of these compounds have naturally been unknown.

DISCLOSURE OF INVENTION

The present inventors have researched the action of microorganisms belonging to Acremonium sp., e.g. a strain of mold fungi, in a substrate of 4-pregnene- 3,20-dione. As a result, it has been found that two types of novel pregnene derivatives specified in this invention are produced.

The present inventors have further subjected one of the derivatives produced above to a reaction with acid anhydrides and found that esters of these derivatives can be obtained.

The pregnene derivatives of this invention can be used as intermediates for the manufacture of - TM progesterone derivatives. These pregnene derivatives including the above mentioned esters exhibit also cell differentiation activity.

The pregnene derivatives of this invention are specified in claim 1, and representative examples of these derivatives have the following chemical names.

7β,15β,17α-Trihydroxy-4-pregnene-3,20-dione (the 1st compound of this invention described in claim 2).

7β-Hydroxy-4-pregnene-3,15,20-trione (the 2nd compound of this invention described in claim 3).

BRIEF DESCRIPTION OF DRAWINGS

FIG. 1 illustrates an EI mass spectrum. FIG. 2 shows an infrared absorption spectrum. FIG. 3 shows a proton nuclear magnetic resonance spectrum. FIG. 4 illustrates a $^{13}$C-nuclear magnetic resonance spectrum.

FIG. 5 illustrates an EI mass spectrum. FIG. 6 illustrates a proton nuclear magnetic resonance spectrum. FIG. 7 shows a $^{13}$C-nuclear magnetic resonance spectrum.

BEST MODE FOR CARRYING OUT THE INVENTION

Figure 1:
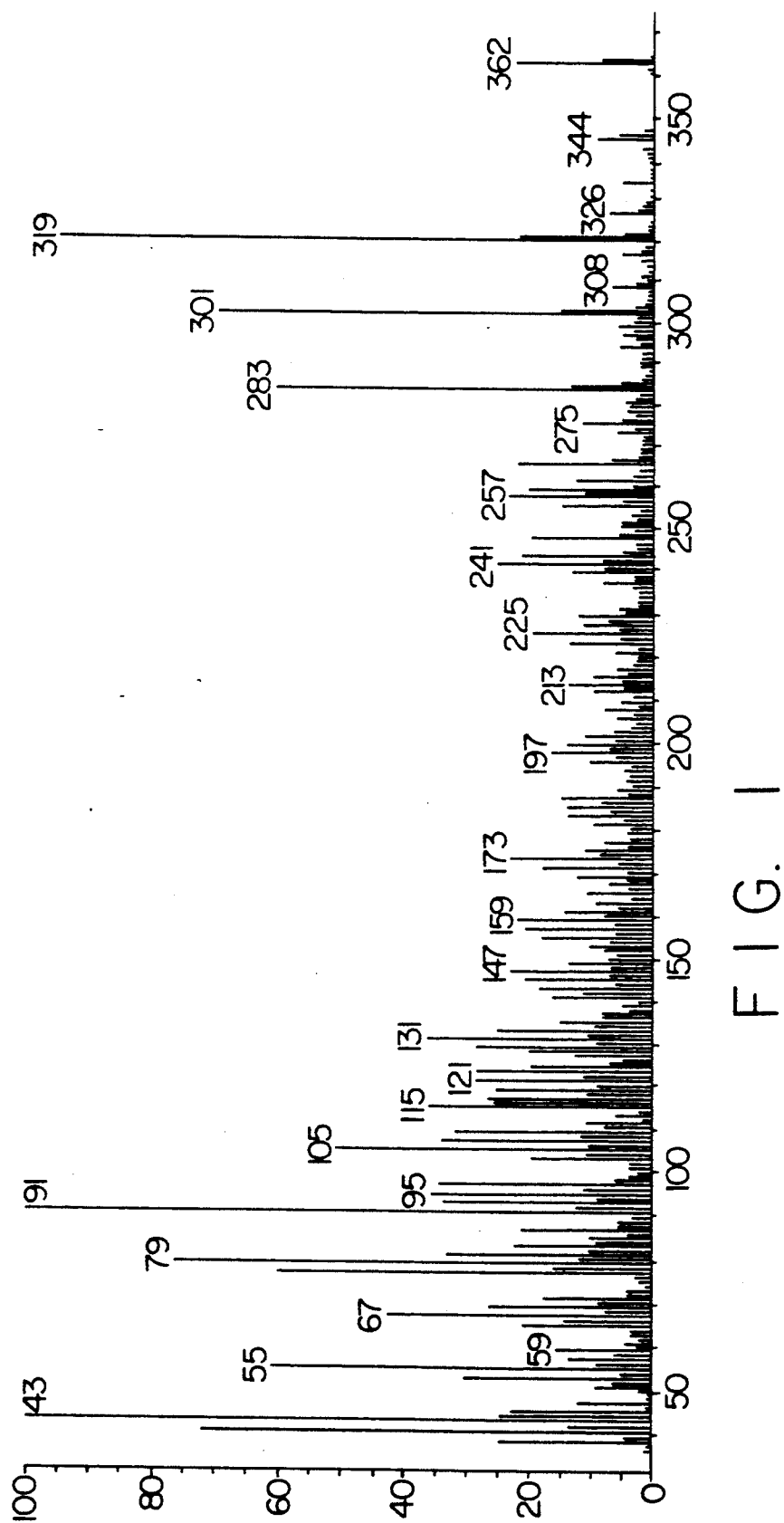
FIGS. 1–4 relate to the 1st compound of this invention.

This invention is to provide a novel pregnene derivatives which is used as an intermediate for the manufacture of progesterone derivatives having progestin activities such as ovulation-inhibiting activity and also has itself cell differentiation activity. This invention will hereinafter be illustrated in detail by way of examples.

Culture of Microorganisms and Conversion of Substrate by the Microorganisms

*Acremonium strictum* NN106 preserved in Hungarian National Institute of Hygiene (FERM P-9143), which is a strain of mold fungi was cultured with shaking in a medium containing carbon sources such as malt extract, peptone, nitrogen sources such as soybean meal, and inorganic salts. In carrying out the culture, the strain was inoculated on 100 ml of a culture medium having, for example, a below described composition in a Erlenmeyer flask of 500 ml volume. The culture was incubated and shaken simultaneously in a incubator with a rotary shaker at a rate of 200 rpm for 48 hours at 24° C.

| | |
|---|---:|
| Malt extract | 30 g |
| Peptone | 20 g |
| Soybean meal | 10 g |
| Potassium phosphate, monobasic | 5 g |
| Magnesium sulfate | 5 g |
| Purified water | 1000 ml |

The above strain was deposited as FERM P-9143 in Fermentation Research Institute of the Agency of Industrial Science and Technology on Jan. 21, 1987.

4-Pregnene 3,20-dione as a substrate was dissolved in dimethylformamide in advance so as to obtain a substrate concentration of 0.1 g/ml.

To the culture solution obtained above, 2 ml of the above substrate solution was added and a reaction was carried out for 24–48 hours under the same conditions as above.

After completing the reaction, solid matters and cells were removed from the resultant culture solution by centrifugal separation. The resultant supernatant was extracted three times, each time using one third of its volume of ethyl acetate. The solvent was removed from the extracted solution with a rotary evaporator.

A crude fraction thus obtained was dissolved in a small amount of chloroform (or methanol) and passed through a silica gel column HPLC (20 mm diameter×300 mm length). The adsorbed fractions were eluted with a solvent mixture (chloroform:methanol=98:2) and fractionated.

The eluate could be divided into at least two fractions. A constituent contained in one of the fractions was identified as 7β,15β,17α-trihydroxy-4-pregnene-3,20-dione (the 1st compound of this invention) by the below described physicochemical properties obtained as a result of structural analysis. The yield was 9.6 mg.

A constituent contained in the other fraction which was eluted earlier than above, for example, at 6 minutes as compared to 26 minutes for the above 1st compound was identified as 7β-hydroxy-4-pregnene-3,15,20-trione (the 2nd compound of this invention) by the same method as above.

7β,15β,17α-Trihydroxy-4-pregnene-3,20-dione is represented by the chemical formula (II):

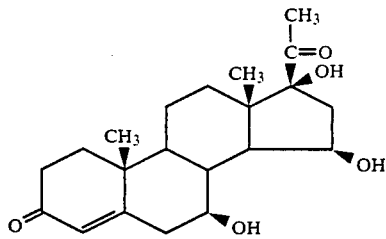

(II)

The compound can be identified by the following physicochemical properties.

Figure 2:
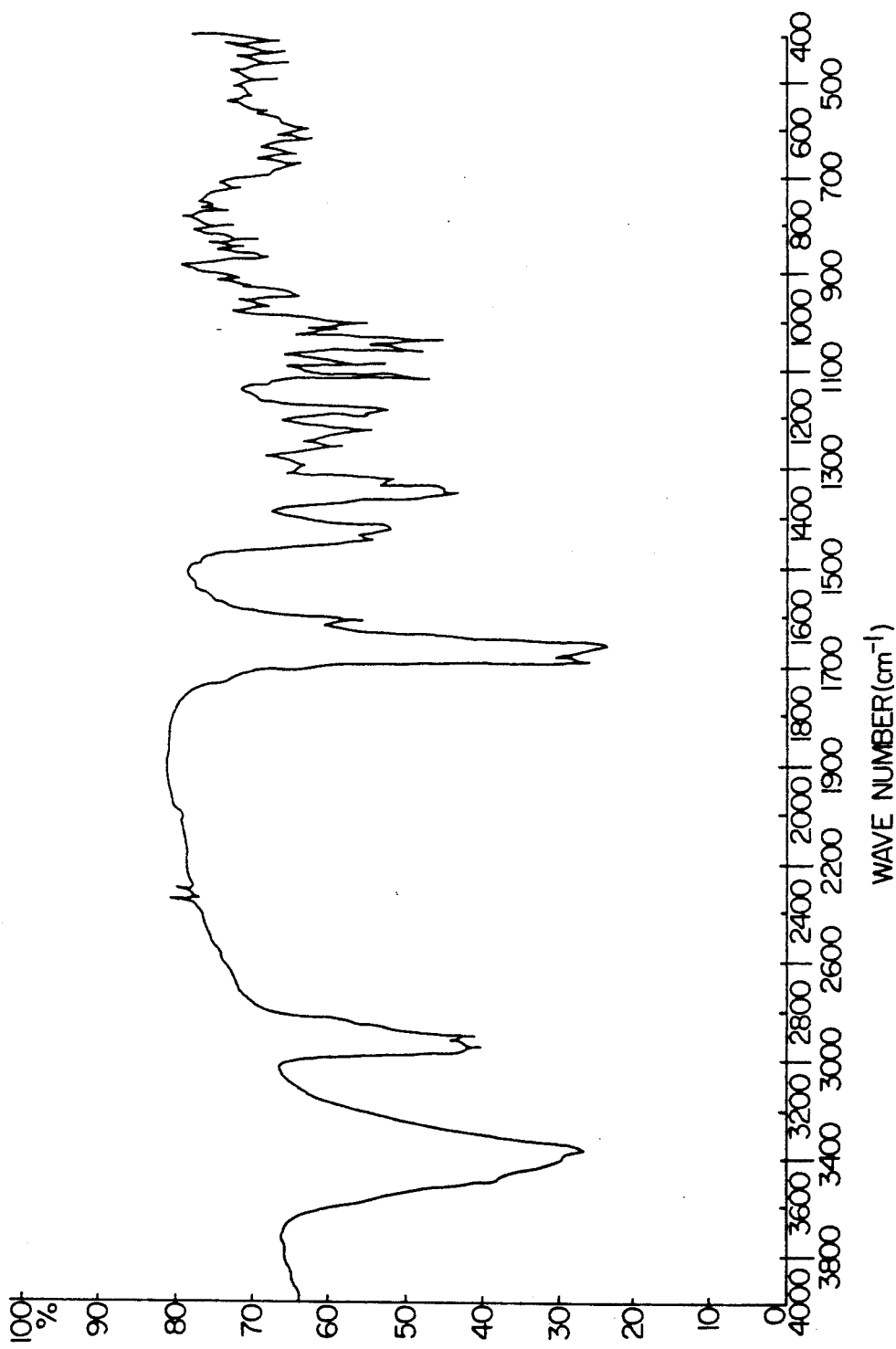
Figure 3:
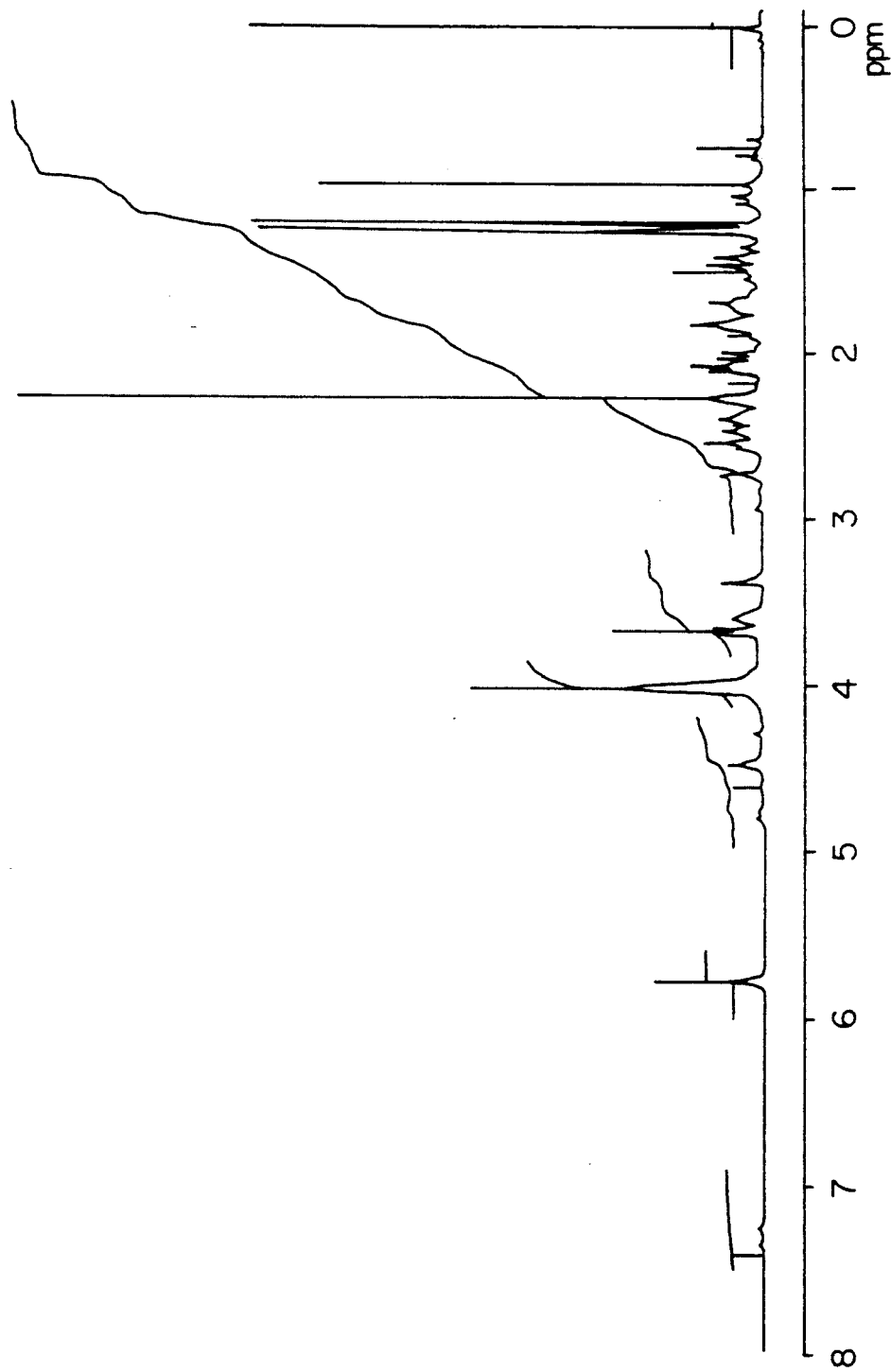
Figure 4:
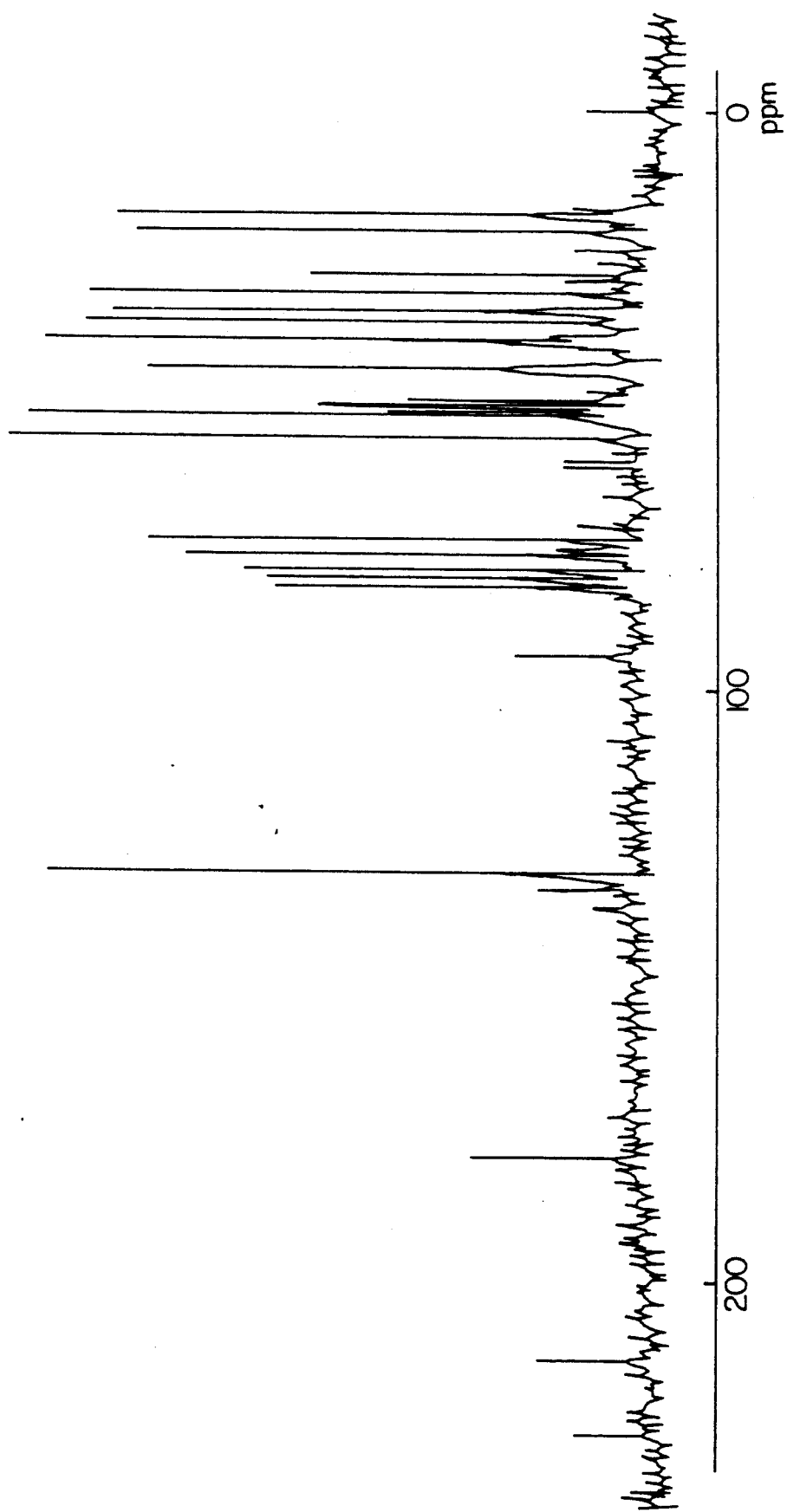

| | | |
|---|---|---|
| (1) | Appearance | White powder |
| (2) | Molecular weight | 362 |
| (3) | Molecular formula | $C_{21}H_{30}O_5$ |
| (4) | Melting point | 248–250° C. |
| (5) | Specific rotation | $[\alpha]D = +41.4°$ |
| (6) | EI mass spectrum | m/Z = 362. See FIG. 1. |
| (7) | Infrared absorption spectrum | See FIG. 2. |
| (8) | Proton nuclear magnetic resonance spectrum | See FIG. 3. |
| (9) | $^{13}$C-nuclear magnetic resonance spectrum | See FIG. 4. |

7β-Hydroxy-4-pregnene-3,15,20-trione is represented by the chemical formula (III):

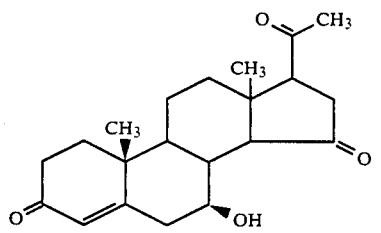

(III)

The compound can be identified by the following physicochemical properties.

Figure 5:
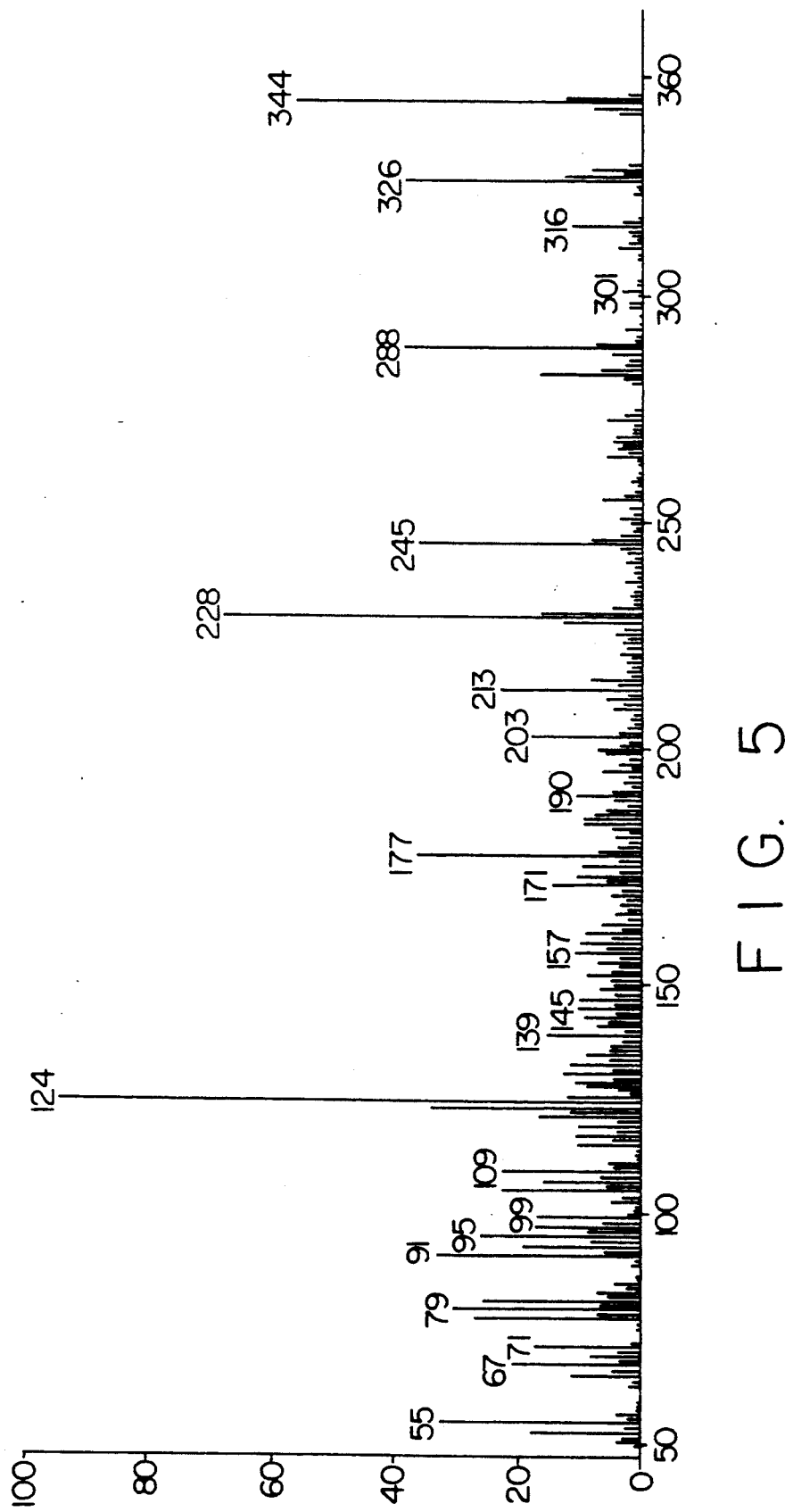
FIGS. 5–7 relate to the 2nd compound of this invention.
Figure 6:
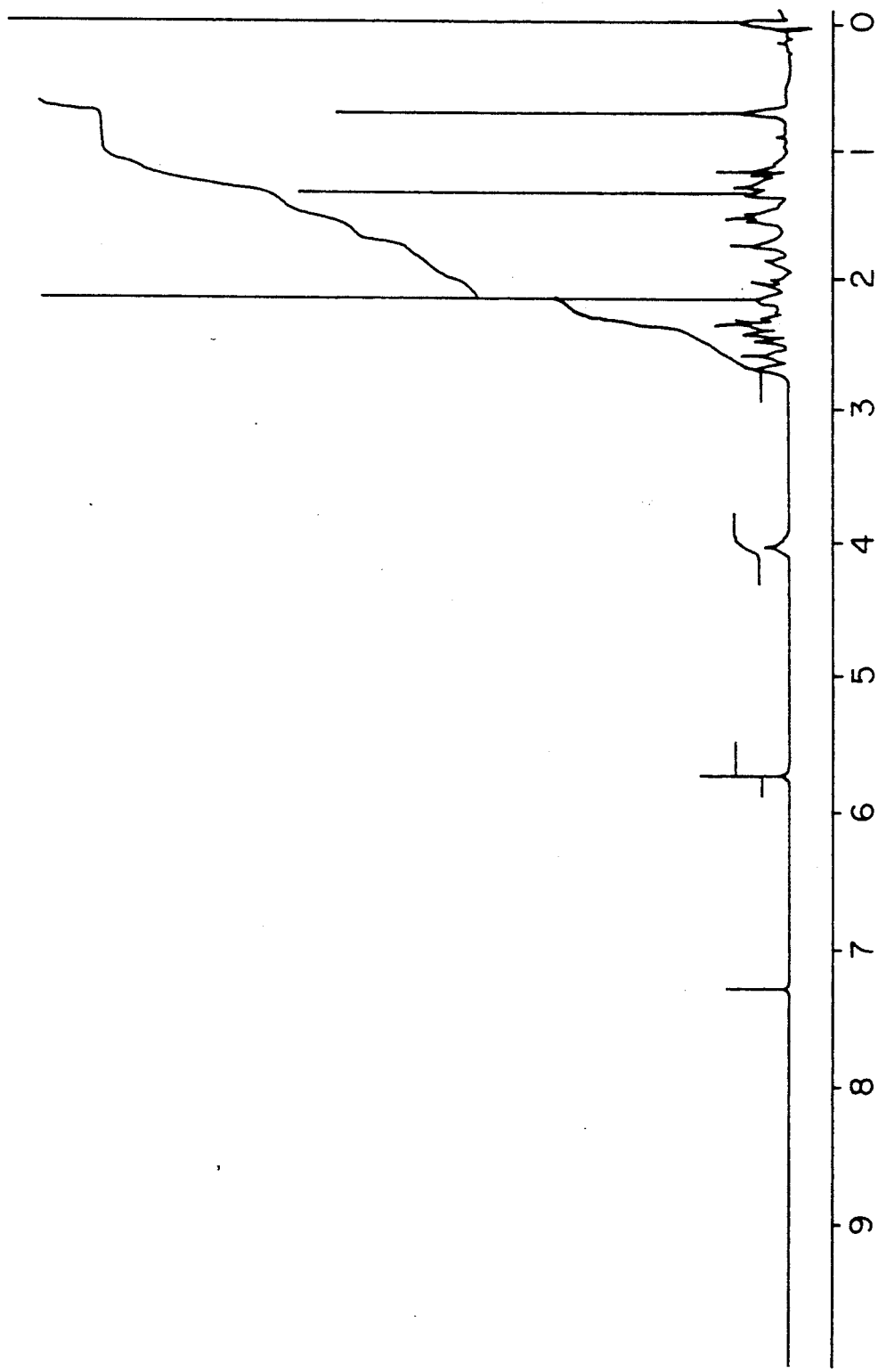
Figure 7:
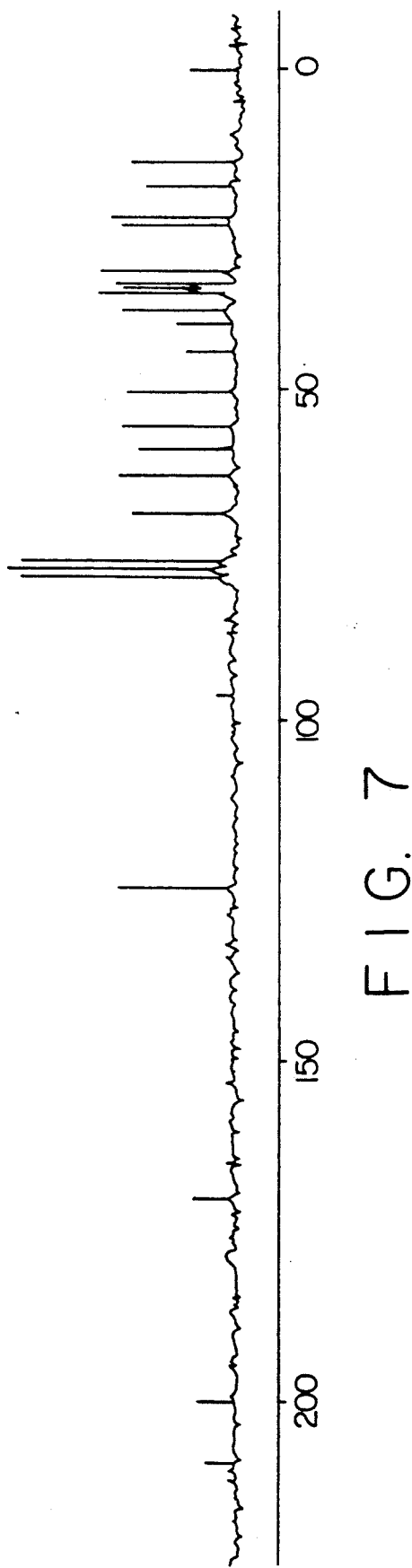

| | | |
|---|---|---|
| (1) | Appearance | White powder |
| (2) | Molecular weight | 344 |
| (3) | Molecular formula | $C_{21}H_{28}O_4$ |
| (4) | Melting point | 254–256° C. |
| (5) | EI mass spectrum | m/Z = 344, See FIG. 5. |
| (6) | Proton nuclear magnetic resonance spectrum | See FIG. 6. |
| (7) | $^{13}$C-nuclear magnetic resonance spectrum | See FIG. 7. |

INDUSTRIAL APPLICABILITY

Preparation of Ester Derivative

7β,15β,17α-Trihydroxy-4-pregnene-3,20-dione is used as an intermediate for the synthesis of progesterone derivatives having ovulation-inhibiting activity as illustrated below. For example, 7β,15β-diacetyl-17α-hydroxy-4-pregnene-3,20-dione can be prepared by using the compound as the intermediate according to the below described procedures. That is, the compound is reacted with acetic anhydride in pyridine to give the above acetylated derivative in the yield of 96%.

In accordance with the above mentioned procedures, disuccinic acid ester derivative or diglutaric acid ester is obtained respectively by reacting succinic anhydride or glutaric anhydride in place of acetic anhydride. Test of cell differentiation activity:

The below described compounds were respectively allowed to act for 48 hours on myelogenic leukemia M1 cells derived from SL mouse.

The cell differentiation activity was measured by observing morphological change of the cells under a microscope. The results are indicated in Table 1.

TABLE 1

| Test compound | Cell Differentiation activity |
|---|---|
| 7β,15β,17α-Trihydroxy-4-pregnene-3,20-dione (the 1st compound of this invention) | + + |
| 7β,15β-Diacetyl-17α-hydroxy-4-pregnene-3,20-dione | + |
| 7β,15β-Discuccinyl-17α-hydroxy-4-pregnene-3,20-dione | + |
| 7β,15β-Diglutaryl-17α-hydroxy-4-pregnene-3,20-dione | + |

7β-Hydroxy-4-pregnene-3,15,20-trione also exhibits cell differentiation activity to some extent on the M1 cells derived from mouse as indicated in Table 2.

TABLE 2

| Cell differentiation activity on M1 cells | |
|---|---|
| Progesterone | — |
| 7β-Hydroxy-4-pregnene-3,15,20-trione | 50% |

Reference to microorganisms deposited pursuant to Regulation 13 bis.

Deposit Organization: Fermentation Research Institute of the Agency of Industrial Science and Technology Address: 1-3, Higashi-1-chome, Tsukuba-shi, Ibaraki-ken, JAPAN Deposit No.: FERM P-9143

Date of Deposit: Jan. 21, 1987

We claim:

1. A method for preparing 7β,15β,17α-trihydroxy-4-pregnene-3,20-dione of the formula:

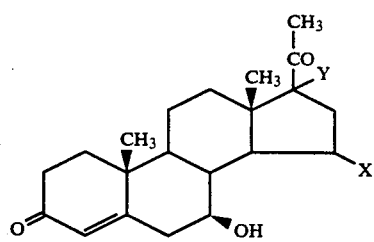

wherein X is αHβOH, and Y is αOH, which comprises contacting 4-pregnene-3,20-dione with a microorganism having all of the identifying characteristics of the strain *Acremonium strictum* NN106 and isolating 7β,15β,17α-trihydroxy-4-pregnene-3,20-dione.

2. A method for preparing 7β-hydroxy-4-pregnene-3,15,20-trione of the formula:

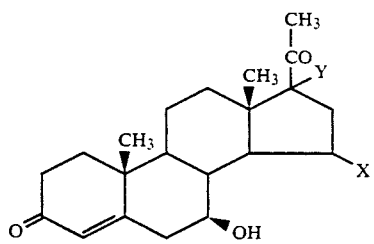

wherein X is =O and Y is αH, which comprises contacting 4-pregnene-3,20-dione with a microorganism having all of the identifying characteristics of the strain *Acremonium strictum* NN106 and isolating 7β-hydroxy-4-pregnene-3,15,20-trione.

* * * * *

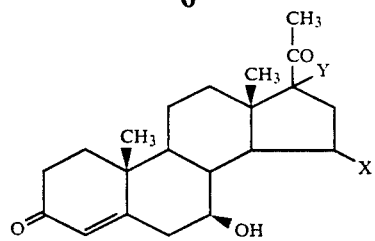

wherein X is =O and Y is αH, which comprises contacting 4-pregnene-3,20-dione with a microorganism having all of the identifying characteristics of the strain *Acremonium strictum* NN106 and isolating 7β-hydroxy-4-pregnene-3,15,20-trione.

* * * * *